US011826306B2

(12) United States Patent
Rifai et al.

(10) Patent No.: US 11,826,306 B2
(45) Date of Patent: Nov. 28, 2023

(54) DEVICE AND COMPUTER PROGRAM FOR TRAINING A PREFERRED RETINAL LOCUS OF FIXATION

(71) Applicant: Carl Zeiss Vision International GmbH, Aalen (DE)

(72) Inventors: Katharina Rifai, Tübingen (DE); Siegfried Wahl, Donzdorf (DE); Maria Barraza-Bernal, Entringen (DE)

(73) Assignee: Carl Zeiss Vision International GmbH, Aalen (DE)

( * ) Notice: Subject to any disclaimer, the term of this patent is extended or adjusted under 35 U.S.C. 154(b) by 181 days.

(21) Appl. No.: 15/856,974

(22) Filed: Dec. 28, 2017

(65) Prior Publication Data
US 2018/0116900 A1 May 3, 2018

Related U.S. Application Data

(63) Continuation of application No. PCT/EP2016/064848, filed on Jun. 27, 2016.

(30) Foreign Application Priority Data

Jun. 29, 2015 (EP) .................................... 15001911

(51) Int. Cl.
*A61H 5/00* (2006.01)
*A61B 3/00* (2006.01)
(Continued)

(52) U.S. Cl.
CPC ............. *A61H 5/00* (2013.01); *A61B 3/0091* (2013.01); *A61H 99/00* (2013.01); *G09B 5/02* (2013.01);
(Continued)

(58) Field of Classification Search
CPC .. A61H 5/00; A61H 99/00; A61H 2201/5043; G09B 5/02; A61B 3/0091; A61B 3/113; A61B 3/024; A61B 3/02
(Continued)

(56) References Cited

U.S. PATENT DOCUMENTS 4,544,246 A * 10/1985 Crane .................... A61B 3/113
351/210
5,035,500 A * 7/1991 Rorabaugh ............ A61B 3/024
351/224
(Continued)

FOREIGN PATENT DOCUMENTS

CN    1617698 A    5/2005
CN    100431511 C    11/2008
(Continued)

OTHER PUBLICATIONS

Morales, Marco, "MAIA—Vision Training Module", Wayback Machine date Mar. 31, 2014, download from URL https://web.archive.org/web/20140331173823/https://www.slideshare.net/marcoulises/maia-vision-training-module on Mar. 19, 2019.*
(Continued)

*Primary Examiner* — Michael C Grant
(74) *Attorney, Agent, or Firm* — Tautz & Schuhmacher LLC; Georg M. Hasselmann

(57) ABSTRACT

The disclosure relates to a method and a respective computer program with a program code to execute the method. In particular, disclosed is a method for training a preferred retinal locus of fixation (efficient PRL) for a person having an eye with a field of vision comprising an area of partially diminished or entirely degenerated visual acuity. The method includes: a) determining an inefficient retinal region outside the area in the field of vision of the eye of the person and a more efficient retinal region for the specific vision task outside the area in the field of vision of the eye of the person and b) inducing a preferred retinal locus of fixation (efficient PRL) for a vision task outside the inefficient retinal region but in the more efficient retinal region. In addition, the disclosure relates to a device for performing the method.

15 Claims, 13 Drawing Sheets

(51) Int. Cl.
| | | |
|---|---|---|
| *A61H 99/00* | (2006.01) | |
| *G09B 5/02* | (2006.01) | |
| *A61B 3/024* | (2006.01) | |
| *A61B 3/113* | (2006.01) | |

(52) U.S. Cl.
CPC .............. *A61B 3/024* (2013.01); *A61B 3/113* (2013.01); *A61H 2201/5043* (2013.01)

(58) Field of Classification Search
USPC ........................................................ 434/247
See application file for complete search history.

(56) References Cited

U.S. PATENT DOCUMENTS

| | | | |
|---|---|---|---|
| 6,464,256 B1 | 10/2002 | Edwards | |
| 6,464,356 B1* | 10/2002 | Sabel ..................... | A61B 3/024 351/203 |
| 7,367,671 B2* | 5/2008 | Sabel ..................... | A61B 3/024 351/203 |
| 7,753,524 B2 | 7/2010 | Sabel | |
| 7,901,072 B1 | 3/2011 | Eagan et al. | |
| 8,454,159 B1* | 6/2013 | Cislo ..................... | A61F 9/00 351/159.63 |
| 8,857,987 B2 | 10/2014 | Tanassi et al. | |
| 9,028,067 B1* | 5/2015 | Fleischman ............ | A61B 3/113 351/209 |
| 9,700,202 B2* | 7/2017 | Fateh ..................... | A61B 3/024 |
| 2007/0200927 A1* | 8/2007 | Krenik ................... | A61B 3/032 348/47 |
| 2011/0304821 A1* | 12/2011 | Tanassi .................. | A61B 3/12 351/206 |
| 2014/0028976 A1* | 1/2014 | Tanassi .................. | A61B 3/152 351/208 |
| 2015/0250583 A1* | 9/2015 | Rosen .................... | A61B 3/14 623/6.23 |
| 2017/0084203 A1* | 3/2017 | Aguren .................. | A61H 5/00 |
| 2018/0104106 A1* | 4/2018 | Lee ........................ | A61F 9/08 |
| 2018/0116900 A1* | 5/2018 | Rifai ..................... | A61B 3/0091 |

FOREIGN PATENT DOCUMENTS

| | | |
|---|---|---|
| WO | 2010/129711 A1 | 11/2010 |
| WO | 2013/050926 A1 | 4/2013 |
| WO | 2015/022514 A1 | 2/2015 |

OTHER PUBLICATIONS

Morales, et al, "Augmented reality eyewear for home-based vision training after biofeedback rehabilitation of eccentric fixation." conference paper, May 2015.*
URL https://www.researchgate.net/publication/279447794_Augmented_reality_eyewear_for_home-based_vision_training_after_biofeedback_rehabilitation_of_eccentric_fixation on Mar. 20, 2019.*
Lad, et al, "Evaluation of visual function impairments in patients with dry age-related macular degeneration", iovs, Apr. 2014, downloaded from URL https://iovs.arvojournals.org/article.aspx?articleid=2270801 on Mar. 20, 2019.*
Stuart, Annie, "Expanded Role for Microperimetry in Visual Rehabilitation", Eyenet, Apr. 2013.*
Crossland et al.: "The Preferred Retinal Locus in Macular Disease: Toward a Consensus Definition," Retina, Nov. 2011; 31(10); pp. 2109-2114.
Kwon et al.: "Rapid and persistent adaptability of human oculomotor control in response to simulated central vision loss," Current Biology, 23(17); pp. 1663-1669, Sep. 9, 2013.
MAIA: "The New Frontier of Microperimetry," Product information brochure, Centervue, available at: www.centervue.com/products/maia/, downloaded Sep. 26, 2017.
MAIA: "Microperimetry Handbook," first edition, 2015.
MAIA: Online presentation "MAIA Vision Training Module," 42 slides, available at: de.slideshare.net/marcoulises/maia-vision-training-module, last accessed Jan. 17, 2018.
MAIA: Youtube video: "Centervue MAIA PRL fixation training," available at: www.youtube.com/watch?v=Q1JQBCGHpRU&feature=youtu, 6 sample slides provided, last accessed Jan. 17, 2018.
Morales et al.: "Bilateral eccentric vision training on pseudovitelliform dystrophy with microperimetry biofeedback," BMJ Case Rep 2015. doi:10.1136/bcr-2014-207969.
Extended European Search report of EP15001911.5, from which this application claims priority, dated Dec. 9, 2015.
International Search Report of PCT/EP2016/064848, from which this application claims priority, dated Sep. 26, 2016.
Written Opinion issued in PCT/EP2016/064848, from which this application claims priority, dated Sep. 26, 2016.
International Preliminary Report on Patentability issued in PCT/EP2016/064848, from which this application claims priority, dated Jan. 2, 2018.
Intention to grant European patent application EP15001911.5 dated Feb. 20, 2017.
Decision to grant European patent application EP15001911.5 dated Jul. 13, 2017.
Machine translation and Office action by the State Intellectual Property Office of P.R. China issued in CN 2016800389604, which is a counterpart hereof, dated Aug. 14, 2018.
Office action by the Chinese Patent Office (SIPO) issued in CN 201680038960.4, which is a counterpart hereof, dated Sep. 26, 2019, and English-language translation thereof.
Office action by the Chinese Patent Office (SIPO) issued in CN 201680038960.4, which is a counterpart hereof, dated Jun. 3, 2019, and English-language translation thereof.
Office action by the Chinese Patent Office (SIPO) issued in CN 201680038960.4, which is a counterpart hereof, dated Feb. 20, 2019, and English-language translation thereof.
Office action by the Chinese Patent Office (SIPO) issued in CN 201680038960.4, which is a counterpart hereof, dated Jan. 19, 2020, and English-language translation thereof.

* cited by examiner

FIG. 9A
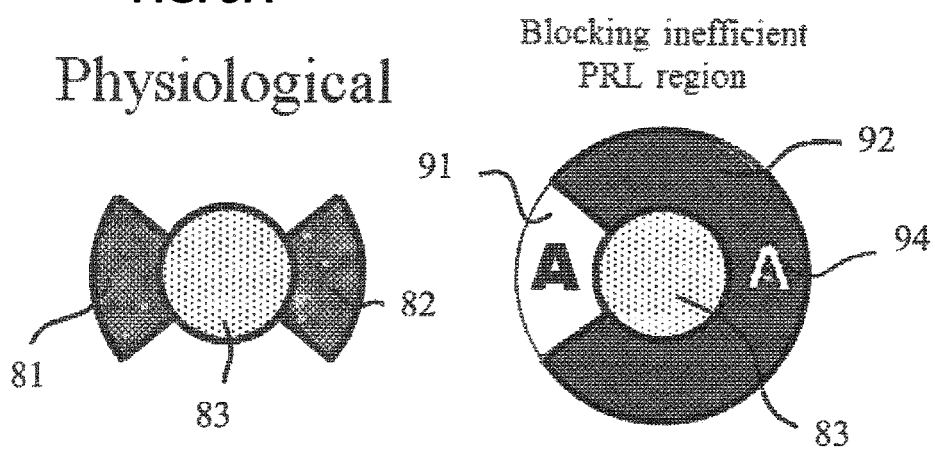
FIG. 9B
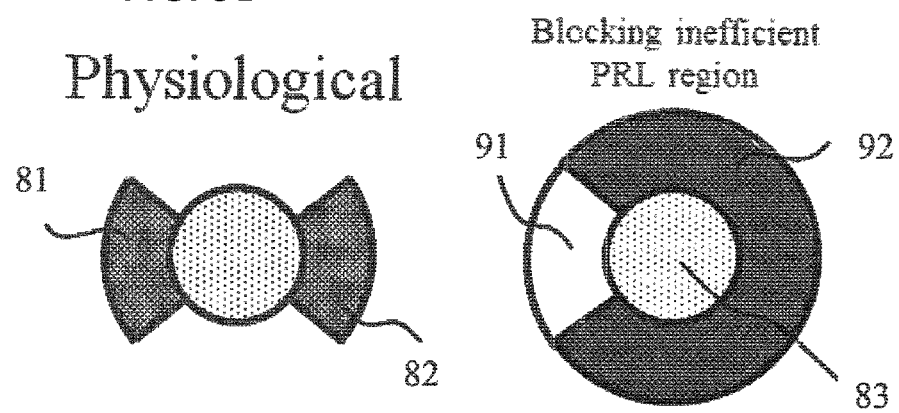
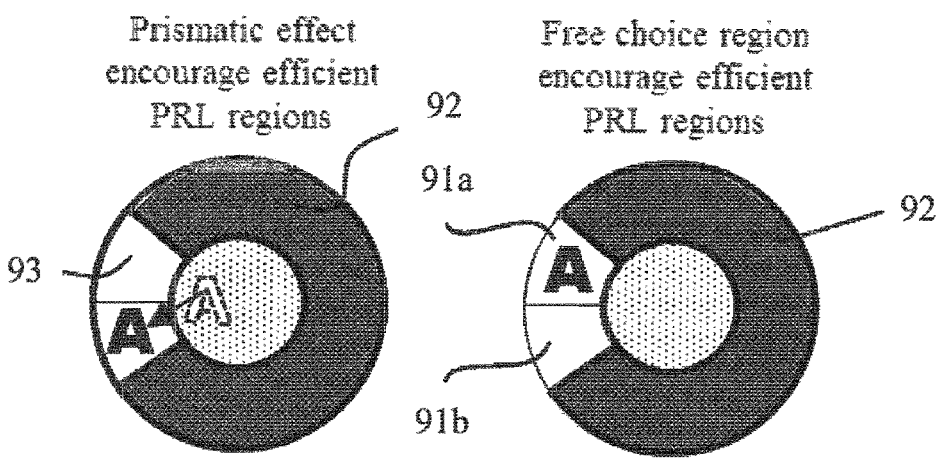

FIG. 9C
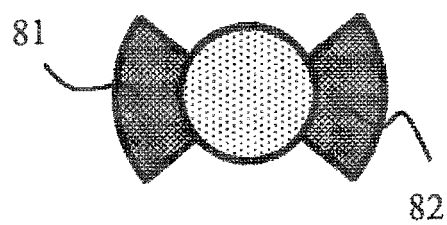
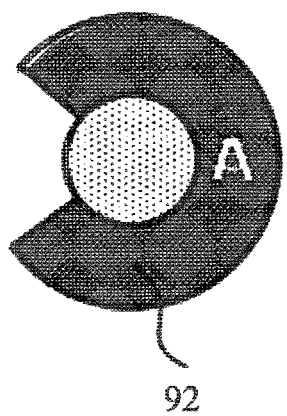
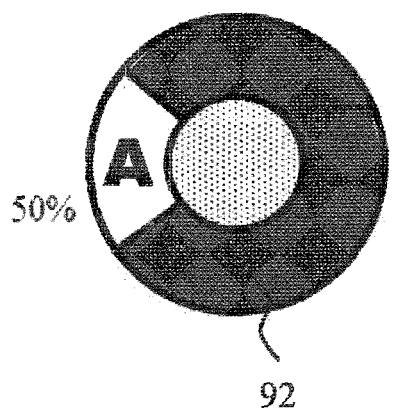

FIG. 15
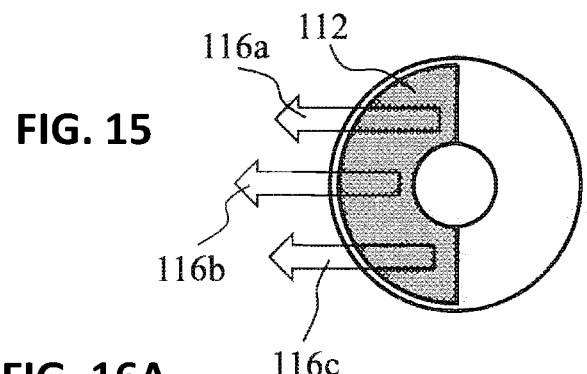
FIG. 16A FIG. 16B
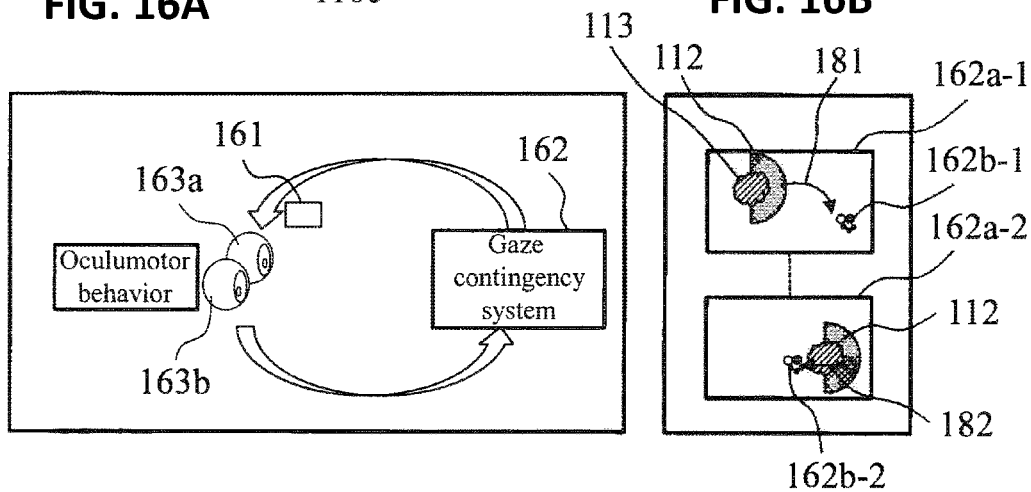
FIG. 17A
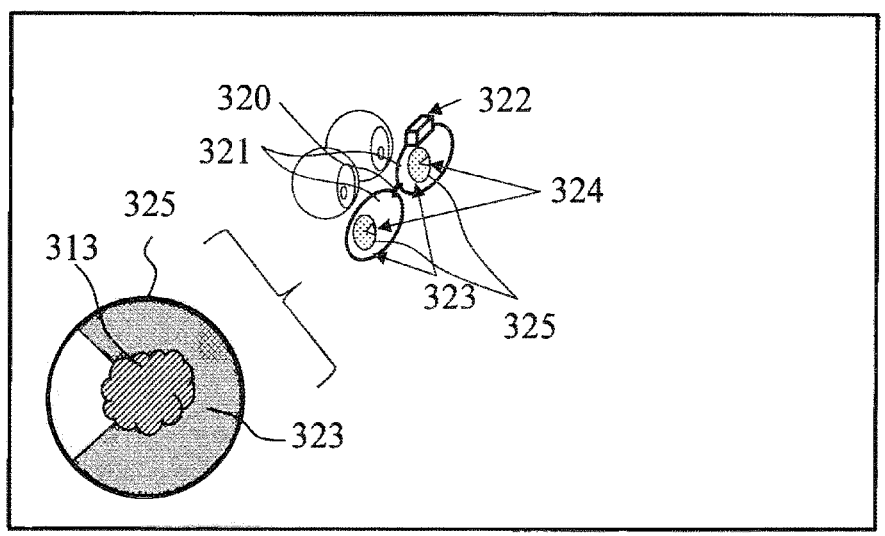

DEVICE AND COMPUTER PROGRAM FOR TRAINING A PREFERRED RETINAL LOCUS OF FIXATION

CROSS-REFERENCE TO RELATED APPLICATIONS

This application is a continuation application of International Application No. PCT/EP2016/064848 filed on Jun. 27, 2016 and designating the United States, and claims priority to European patent application EP 15001911.5 filed on Jun. 29, 2015, both of which are hereby incorporated by reference in their entireties as if fully set forth herein.

TECHNICAL FIELD

The disclosure relates to a computer program with program code to execute a method of training an efficient preferred retinal locus of fixation and a device for training an efficient preferred retinal locus of fixation.

BACKGROUND

As explained, for example, by Kwon et al. in "Rapid and persistent adaptability of human oculomotor control in response to simulated central vision loss," Current Biology, 2013 Sep. 9; 23(17): 1663 to 1669, the central region of the human retina, the fovea, provides high-acuity vision. The oculomotor system continually brings targets of interest into the fovea via ballistic eye movements (saccades). The fovea thus serves both as the locus for fixations and as the oculomotor reference for saccades.

There are persons who suffer from scotoma, in particular central scotoma. A scotoma is an area of partial alteration in the field of vision consisting of a partially diminished or entirely degenerated visual acuity that is surrounded by a field of normal or relatively well-preserved vision. Scotoma is a symptom of damage to any part of the visual system, such as retinal damage from exposure to high-powered lasers, direct sunlight, macular degeneration, or brain damage.

Central scotoma (or central vision loss) is one of the visually most restrictive indications in vision loss. Central vision loss might occur due to a variety of reasons such as Stargadt's disease or macular degeneration. The majority of cases occurs due to macular degeneration. Although the disclosure is applicable for all kinds of scotoma, for demonstration purposes the disclosure is explained with reference to typical macular degeneration caused defects of the eye.

Macular degeneration, often age-related macular degeneration (abbreviated AMD or ARMD), is a medical condition that usually affects older adults and results in a loss of vision in the center of the visual field (the macula) because of damage to the retina. Approximately 10% of person/probands 66 to 74 years of age will have findings of macular degeneration. The prevalence increases to 30% in person/probands 75 to 85 years of age.

The loss of central vision profoundly affects visual functioning. It is quite difficult, for example, to read without central vision. Pictures that attempt to depict the central visual loss of macular degeneration with a black spot do not really do justice to the devastating nature of the visual loss.

FIG. 1 shows a drafted picture of two children 1, 2, each having a ball 3, 4 in its hands 8, 9. The children's 1, 2 heads 5, 6 are located in front of a wooden fence 7. The picture according to FIG. 1 represents a situation as perceived by a person without any visual loss. FIG. 2 shows a picture of the same situation as perceived from a person with central vision loss due to macular degeneration. The heads 5, 6 of the children 1, 2 have vanished completely, which is indicated by a dark cloud 10. The environment surrounding the cloud 10 being represented by the balls 3, 4, the hands 8, 9 and the fence 7 may be more or less blurred but still visible.

Although there are several promising treatments of AMD under consideration, all of them only aim at slowing down the progression or stopping the progression of AMD. The vision, which is already lost cannot be restored. Person/probands with central vision loss have to learn to use another part of the retina for fixation. Kwon et al. describe this cognitive process as the oculomotor system having to adopt a peripheral locus for fixation and to re-reference saccades to this locus.

Until now, the person/proband had to learn to use another eccentric location of the retina as a new locus for fixations and to guide their eye movements in a self-paced way. This is very cumbersome because the eye movement system is naturally trained to bring a target onto the fovea. The other location of the retina used as a new locus for fixations in literature is called as preferred retinal locus (PRL) for fixation. According to Crossland et al., "The preferred retinal locus in macular disease: toward a consensus definition." in Retina; 2011 November; 31 (10): 2109-2114, the PRL is characterized in that 1) it is a retinal area used for fixation, 2) it is task specific, 3) more than one PRL can be used, 4) it is a well-defined region of the retina, and 5) the same PRL is used on repeated testing.

It is known that the exact position of the PRL should be decided upon based on its efficiency. In particular, it should be placed as close as possible to the fovea and it should be selected based on the specific vision task. These two prerequisites for the efficiency of a PRL are explained in more detail in the following:

1. Proximity of the PRL to the Fovea

FIG. 3 shows a plan view of the visual field 11 of a human retina of a person having a central scotoma due to macular degeneration. The outer ring 12 indicates the outer contour of the visual field 11 of the retina. The cloud 13 indicates the area of vision loss. Reference number 16 indicates the outer contour of the area of vision loss 13.

The person having the central scotoma 13 may establish two (or even more) task dependent PRLs 14, 15 as explained, e.g., on page 1666, left col., second paragraph, of Kwon et al. Due to the decaying acuity in the periphery of the retina away from the fovea centralis, the acuity at the location of PRL 15 exceeds the acuity at the location of PRL 14. Thus, PRL 15 is more efficient than PRL 14. Therefore, in the following a PRL of the type of PRL 14 is called non-efficient PRL and a PRL of the type of PRL 15 is called efficient PRL.

2. Task Dependency of the PRL

The above assumption that a PRL being closer to the fovea is more efficient than a PRL being further away from the fovea in the periphery of the retina is, e.g., valid for a face recognition task (see, e.g., a situation according to FIG. 2). This may not necessarily be valid for a reading task as will be explained with reference to FIGS. 4 to 7.

FIG. 4 shows a plan view of the visual field 11 of a human retina of a person having a central scotoma 13 due to macular degeneration and a fixation target 17 represented by a text passage in a book on the right-hand side of the plan view of the visual field 11 of the retina. The outer ring 12 indicates the outer contour of the visual field 11 of the retina.

The cloud 13 indicates the area of vision loss. Reference number 16 indicates the outer contour of the area of vision loss 13.

FIG. 4 assumes that the person has a PRL 18 being located on the left-hand side of the scotoma 13. When starting the reading task, the person will move head and/or eye to position the PRL 18 to the top and left-hand side of the fixation target 17 (the letters "Ma"). The respective movement is indicated by means of arrow 19. The location of the beginning of the text passage at which the PRL 18 is located after head and/or eye movement is indicated with circle 20 in FIG. 4. As a consequence, scotoma 13 will be located at the position of cross 21. FIG. 5 shows the relative positions of the visual field 11 of the human retina and the fixation target 17 after head and/or eye movement 19 have occurred in order to start reading.

The situation shown in FIG. 6 corresponds to the situation shown in FIG. 4 with the difference that the person has a PRL 22 being located on the right-hand side of the scotoma 13. When starting the reading task, the person will move head and/or eye to position the PRL 22 to the top and left-hand side of the fixation target 17. The respective movement is indicated by means of arrow 23. The location of the beginning of the text passage at which the PRL 22 is located after head and/or eye movement is indicated with circle 24 in FIG. 6. As a consequence, scotoma 13 will be located at the position of cross 25. FIG. 7 shows the relative positions of the visual field 11 of the human retina and the fixation target 17 after head and/or eye movement 23 have occurred in order to start reading.

A PRL 22 using the visual field to the right of the fovea is especially efficient in reading. When moving the eyes from word to word from left to right, an eye movement 23 to a word has only to be kept shorter, whereas a PRL 18 using the left visual field from the fovea would require to make an eye movement 19 over the fixation target 17. Therefore, the PRL 22 to the right of the fovea is more efficient than the PRL 18 to the left of the fovea.

Since during eye movement the complete line of an actually read text passage is visible if a PRL below the fovea is used (not shown here), the PRL below the fovea is even more efficient than PRL 22. This has already been found by Kwon et al., see, in particular, p. 1665, right col., first paragraph, $4^{th}$ line.

In the current, above-explained self-trained way, the above-mentioned benefits cannot be considered, because the choice of PRL does more or less depend on chance and habitual behavior. In addition, a person may establish more than one PRL.

In order to overcome the latter drawback, Kwon et al. propose an explicit training for refinement of a fixational PRL, i.e., to stabilize a self-trained PRL. Kwon et al. displayed a small white cross at the retinal location of each subject's emerged fixational PRL and instructed subjects to follow the target with this gaze marker. In addition, Kwon et al. propose to superimpose a simulated scotoma over a real scotoma to provide accurate positional feedback and speed up PRL development.

Kwon et al.'s proposed methods can provide satisfying results in order to train a person in stabilizing one single efficient preferred retinal locus of fixation. However, in cases where the person has established more than one preferred retinal locus of fixation or in cases where the person has established an inefficient PRL there is a need for further improvement.

WO 2010/129711 A1 discloses a system and method for prescribing, evaluating, and optimizing person/proband rehabilitation programs. Using a preferred retinal location approach, a person/proband coping with macular disease, for example, can learn to fixate on a location within his or her visual field of view that exhibits relatively less visual impairment, thus enabling the person/proband to enjoy a more satisfying visual experience. The system's processing engine is used to move a target image off-fovea—i.e., away from the area responsible for central vision—to various selected locations and to generate a map representing the person/proband's relative visual acuity at each of the selected locations. The system's psychophysics testing component can be performed in parallel to also move a target image off-fovea to varying locations and to solicit person/proband responses for each of the varying locations, in order to map the person/proband's relative visual acuity at each of the varying locations. The results of the parallel mapping can be correlated, and the mapped location corresponding to the person/proband's relatively best vision is selected as the preferred retinal location. The person/proband is then placed in a training program that includes a series of exercises to help train the person/proband's viewing habits such that their visual focus is shifted off-fovea (or off-center) and on the newly selected preferred retinal location. As a result of the training exercises, the person/proband's visual cortex will develop and expand to process stimuli from this new location that is being used as the primary focal point for perceiving images. Periodic modeling and testing can be performed to evaluate the effectiveness of the training program. The training program can be modified based on the modeling and testing results, in order to yield optimal rehabilitation results in the person/proband.

U.S. Pat. No. 7,901,072 B1 describes in col. 1, lines 26 to 42 similar to Kwon et al. that some visually-impaired persons overcome their AMD, Retinitis Pigmentosa, or Diabetic Retinopathy caused impaired vision within their field of view by training themselves to view objects at an angle, e.g., by looking at things out of the corner of their eyes. In addition, U.S. Pat. No. 7,901,072 B1 describes that many devices and procedures have been developed with the goal of alleviating the loss of sight resulting from macular degeneration and other vision impairments. In particular, this citation discloses that prism correction has been added to prescription lenses of glasses for individuals with impaired vision to direct a viewed image to functioning or preferred portions of the retina. The required prism is determined by a subjective refraction using discrete steps of prism diopter and base, and once prescribed, the prism is built into the glasses.

Other, according to U.S. Pat. No. 7,901,072 B1 more extreme measures for correcting visual impairments include vision correction implants that incorporate miniature telescopes. Such telescopes arc implanted directly into an afflicted eye to project an image larger on a person's eye, such that the larger image is viewable at more positions on the eye.

As an improvement of such prism corrected glasses U.S. Pat. No. 7,901,072 B1 discloses an ocular device which includes first and second prisms which may be used without or in combination with a video display device. In case it is used without a video display device may be a hand-held device that allows a user to view his/her surroundings merely by holding the device in front of the eye. The first and second prisms are sufficiently spaced that the first and second prisms move relative to each other. In one embodiment, the first prism is a rotatable prism that is fully rotatable by the user by contacting a first ring. It is beneficial, however, to make the second indexing prism movable to steer the image exiting the first prism. By continuously rotating the rotatable prism, and thus indexing the indexing prism, the ocular device allows for steering of the image through much if not all of the user's field of view. Specifically, in this above cited embodiment, the ocular device's design is optimized to present images to a healthy part of the retina with normal vision.

As an alleged improvement as compared to the device disclosed in U.S. Pat. No. 7,901,072 B1 the publication of the international patent application WO 2013/050926 A1 discloses a lens for people having a visual deficit in one or both the eyes comprising at least one magnifying portion and at least one prismatic portion with a predetermined prismatic element and a predetermined orientation, which orientation corresponds to an angle of rotation or of positioning of the prismatic element about an axis of rotation. The prismatic element is rotated and/or rotatable by a predetermined angle about an axis of rotation, which is parallel and/or coincident with the axis perpendicular to the anatomical frontal plane of the lens. The angle is defined on the basis of the position of the eccentric preferred retinal locus (PRL) within the parafoveal region in order to facilitate image fixation on the area. In addition, the power of the prismatic element may be changed in order not to displace the PRL in circumferential direction but also in radial direction therefore displacing the PRL in any area of the retina belonging to the eye.

Furthermore, WO 2013/050926 A1 discloses a method for the qualitative and quantitative evaluation of the paracentral visual field, for the identification of the eccentric preferred retinal loci (PRLs) from a distance and of the projection of the scotomatous areas by using at least one lens described above. The qualitative and quantitative evaluation of the paracentral visual field, the identification from a distance of PRLs and of the projection of the scotomatous areas occurs by rotating the prismatic element about the axis of rotation and by changing the power of the prismatic element.

U.S. Pat. No. 9,028,067 B1 describes an electronic device called Relocated Image Virtual Retinal Display (RIVRD) comprising a frame configured to be worn on the head of a human and a video camera mounted on the frame. An area of regard (AR) is viewed and captured by the video camera, and the AR is sent to a controller. In addition, a projector is mounted on the frame, the projector image and direction being controlled by the controller. The AR is transformed by the controller remapped image (RI), and is projected by the projector to an alternate retinal area distinct from a diseased central fovea. The frame further comprises an eye tracker which sends an eye position to the controller. The projector is controlled to maintain the AR on the moving alternate retinal area. A pre-mapped alternate retinal area called the preferred retinal locus (PRL) is stored in the controller, and the projector is directed to the PRL by the controller. The location of a particular person/proband's PRL and surrounding "best remaining vision potential" according to U.S. Pat. No. 9,028,067 B1 is reproducibly discovered and mapped using microperimetry techniques (for example, via use of a scanning laser ophthalmoscope). The PRL, including nearby adjacent areas, discovered and mapped for each specific person/proband, will be the new discrete retinal area that will be used as the point of central fixation for relocated images (RI). The citation explicitly outlines in col. 4, line 24 that the essence of the RIVRD is to artificially redirect and stabilize images, to land on that area of functional healthy retina which includes the PRL rather than the diseased area of lost central vision.

WO 2015/022514 A1 describes that person/probands with age-related macular degeneration and similar conditions affecting the central visual field may still make effective use of residual macular tissue outside the damaged fovea (sometimes referred to as the 'preferred retinal locus' or PRL) although this may require the person/proband to learn to fixate eccentrically—something that is not always easily accomplished. The citation points out that one potential method of improving a person/proband's fixation is to undertake surgery to introduce a device to modify the path of light in the eye such that images are focused on the PRL with or without a magnifying effect. Exemplarily, the citation directs the attention to surgical approaches to the management of poor vision in age-related macular degeneration, which include the implantation of telescopic lenses, in some cases not dissimilar to those employed for use in cataract surgery. Such telescopic devices may be configured in such a way as to provide a magnified image that is focused on an area of healthy macula eccentric to the fovea. Most existing designs for these intraocular devices adopt variations on a Galilean telescope system such that a diverging intraocular lens (IOL) is sited in the eye behind a converging IOL.

The citation itself proposes an intraocular lens system comprising: an anterior light-converging intraocular lens for positioning within the eye and a posterior light-diverging intraocular lens for positioning within the eye posterior to the anterior lens. At least one of the surfaces of the anterior lens or surfaces of the posterior lens is a modified surface which includes a surface aberration which increases the depth of focus of the lens, optimizes image quality and may also provide for a magnified image over a range of retinal eccentricities. Embodiments include the application of diffractive surfaces to one optic or both optics to permit a range of focal points in the eye (and consequently uncorrected distance and near vision) or the application of a Fresnel prism to one or both optics to achieve a prismatic effect and targeting of the PRL.

SUMMARY

The problem addressed by the present disclosure is to provide a method as well as a device for training an efficient preferred retinal locus of fixation not only for persons having already established an adequate preferred retinal locus of fixation, but also for persons who lack any preferred retinal locus of fixation or who have established an inefficient preferred retinal locus of fixation. The training process may also allow guidance of the preferred retinal locus at early stages of its development, e.g., at the beginning of the Macular Degeneration.

Deviating from the related art represented by Kwon et al. training and stabilizing an already established PRL, an object of the present disclosure is to establish an efficient, preferably the most efficient PRL one may think of, by inducing the efficient preferred retinal locus of fixation for a specific vision task. The PRL shall be located in a region or an area outside of an inefficient or non-efficient retinal region.

Concretely, the method for training a preferred retinal locus of fixation for a person having an eye with a field of vision comprising an area of partially diminished or entirely degenerated visual acuity, which is provided by means of a computer program with program code to execute the respective method steps if the computer program is loaded in the computer or executed in the computer is according to the disclosure, the method comprising:

1) Determining an inefficient retinal region for a specific vision task outside the area of partially diminished or entirely degenerated visual acuity in the field of vision of the eye of the person and a more efficient retinal region for the specific vision task outside the area of partially diminished or entirely degenerated visual acuity in the field of vision of the eye of the person inducing a preferred retinal locus of fixation for a vision task outside the inefficient retinal region but in the more efficient retinal region.

2) Inducing the preferred retinal locus of fixation for the vision task outside the inefficient retinal region comprises e.g., measures to encourage the person to move head and/or eye in order to gaze such that the retinal location of fixation of the eye of the person lies outside the inefficient retinal region. Simultaneously and/or alternatively, inducing may comprise any measures to discourage the person to move head and/or eye in order to gaze in a direction such that the retinal location of fixation of the eye of the person lies inside the inefficient retinal region.

The foregoing problem is completely solved by the computer program with program code to execute the method as disclosed herein if the computer program is loaded in the computer or executed in the computer.

The induction of a preferred retinal locus of fixation for the vision task outside the inefficient retinal region may, for example, comprise:
blocking the inefficient retinal region for the specific vision task.

Blocking the inefficient retinal region for the specific vision task has the effect that the person is discouraged from moving eye and/or head, such that the PRL is in the inefficient retinal region for the specific vision task.

The method according to the disclosure may further include:
providing a fixation target for the specific vision task to the person.

Providing a fixation target to the person gives guidance to the person for conducting his or her specific vision task. In addition, flexibility is increased as described below with reference to the drawings.

In addition or alternatively to blocking the inefficient retinal region for the specific vision task, the method according to the disclosure may further comprise:
shifting the fixation target to an unblocked region outside the blocked inefficient retinal region.

A PRL is actively induced at the position most beneficial to the person. This is accomplished by moving the visual information of the fixation target from a less efficient retinal location into a region of an efficient retinal location or into a region being completely outside the visual field.

The principal exploits the fact that eye movements consist of fast, large gaze shifts combined with fixation phases, in which visual information is collected. The point of time when the person/proband chooses the retinal location used for fixation is directly after a gaze shift. If now the fixation target falls within an area of non-efficient PRL, it is shifted either into the preferred region for the development of a PRL or the region outside the visual field encouraging the person to start a new attempt to arrange the fixation target in an unblocked retinal area for developing a PRL by moving his head and/or eye.

In other words, an exemplary embodiment of the method according to the disclosure includes shifting of the fixation target to an unblocked region outside the blocked inefficient retinal region including:
shifting the fixation target from the blocked inefficient retinal region to an efficient retinal region in order to encourage the person to develop a PRL in the efficient area of the visual field.

According to another exemplary embodiment of the method according to the disclosure, whereby the field of vision having a foveal region is characterized in that the step of shifting the fixation target to an unblocked region outside the blocked inefficient region comprises: shifting the fixation target from the blocked inefficient region away from the foveal region in order to discourage a non-efficient PRL, thus encouraging the person/proband to place the fixation target in the area of an efficient PRL.

In another exemplary embodiment, the visual information from the fixation target may not be shifted. It may be blocked in a ring-shaped area around the field of vision loss, thus encouraging the person to place the fixation target in the area of an efficient PRL. The exact shape of the ring, in particular its thickness and the open angle, may vary. Thus, even a pinhole-like unblocked region may remain in the field of vision.

In an exemplary embodiment of the disclosure the method may comprise:
tracking a gaze of the eye during conducting the specific vision task, and
determining the inefficient retinal region to be blocked based on the tracked gaze and/or
determining the region to which the fixation target is to be shifted based on the tracked gaze.

The use of gaze tracking, i.e., using a so-called eye-tracker, allows the implementation of the method in a gaze-contingent training tool. In this gaze-contingent training tool, the person may perceive stimuli, such as several symbols, well-separated letters or short words, on a display. Dependent on the tracked gaze, the stimuli (fixation target) may vanish (be blocked) or may occur at another location of the display (be shifted).

In one exemplary embodiment of the disclosure, the method may be comprise
determining an inefficient retinal region in the field of vision of the eye of the person for the specific vision task including:
determining an efficient retinal region in the field of vision of the eye of the person for the specific vision task, and
setting a region outside the efficient retinal region in the field of vision of the eye of the person for the specific vision task as defining the inefficient retinal region in the field of vision of the eye of the person for the specific vision task.

This exemplary embodiment leaves no choice to the person to establish a PRL than the efficient retinal region in the field of vision of the eye of the person for the specific vision task being pre-determined by the operator of the training tool or the operator guiding the person through the training procedure.

Still another exemplary embodiment of the disclosure may comprise blocking the inefficient retinal region when providing the fixation target to the person for conducting the specific vision task by:
hiding a region of the fixation target corresponding to the inefficient retinal region when providing the fixation target to the person for conducting the specific vision task,
exclusively revealing a region of the fixation target corresponding to a region outside the inefficient retinal region when providing the fixation target to the person for conducting the specific vision task, and
exclusively presenting a region of the fixation target corresponding to a region outside the inefficient retinal region when providing the fixation target to the person for conducting the specific vision task.

These features provide alternatives how to realize the previously described blocking.

In order to provide a well-defined shape of the area of the central vision loss to the person the method according to the disclosure may comprise:
at least partially blocking the area of entirely degenerated visual acuity, preferably fully blocking the area of entirely degenerated visual acuity. This measure increases the velocity of establishing a PRL.

It is herewith explicitly outlined that the method and any exemplary embodiment thereof described above may be or is computer-implemented. In particular, according to the disclosure there may be or is a computer program with a program code to execute the method according to the embodiments described in detail above, if the computer program is loaded in the computer and/or executed in the computer.

The computer program may be stored on a non-transitory storage medium.

The main concept for a training tool, in particular to conduct a method described in detail above, is outlined in the following paragraphs.

The inventive device for training a preferred retinal locus of fixation for a person having an eye with a field of vision comprising an area of partially diminished or entirely degenerated visual acuity includes:
an inducing arrangement for inducing a preferred retinal locus of fixation for a specific vision task outside an (predetermined) inefficient retinal region for the specific vision task outside the area of partially diminished or entirely degenerated visual acuity in the field of vision of the eye of the person but onto a predetermined more efficient retinal region for the specific vision task outside the area of partially diminished or entirely degenerated visual acuity in the field of vision of the eye of the person.

Such a device completely solves the problem outlined above.

One exemplary embodiment of a device according to the disclosure may include at least one of:
a gaze dependent blocking arrangement for blocking an area of the visual field dependent on direction of gaze of the eye, and/or
a gaze dependent shifting arrangement for shifting a fixation target dependent on the direction of gaze of the eye.

Another exemplary embodiment of a device according to the disclosure may include at least one of:
a gaze dependent blocking arrangement for blocking an area of the visual field of the predetermined inefficient retinal region for the specific vision task dependent on direction of gaze of the eye, and/or
a gaze dependent shifting arrangement for shifting a fixation target to an unblocked region outside the predetermined inefficient retinal region for the specific vision task dependent on direction of gaze of the eye.

The shifting may comprise moving a visual information of the fixation target from the predetermined inefficient retinal region for the specific vision task into an efficient retinal region for the specific vision task or into a region being completely outside the visual field.

In case an exemplary embodiment comprises a gaze dependent shifting arrangement for shifting a fixation target dependent on a direction of gaze of the eye, an advantageous variant of the exemplary embodiment may include:
a gaze tracking arrangement for tracking a gaze of the eye during conducting a vision task, and at least one of a control arrangement for controlling the area of the visual field to be blocked based on the tracked gaze of the eye, and/or
a control arrangement for controlling the shifting of the fixation target based on the tracked gaze of the eye.

In another exemplary embodiment, the gaze dependent shifting arrangement may comprise or may consist of a gaze dependent prismatic arrangement. The prismatic arrangement brings the image of the fixation target to the desired retinal location. It shifts the fixation target to the above in connection with the inventive method-described location.

Still another exemplary embodiment of a device according to the disclosure includes at least one of the blocking arrangement and/or the shifting arrangement being detachably fixed to the eye. In particular, a contact lens or an intraocular lens may carry a blocking arrangement and/or a shifting arrangement. The blocking arrangement may be a tinted region on the contact lens or the intraocular lens. The shifting region may be a prism being implemented into the contact lens or the intraocular lens.

A further embodiment of a device according to the disclosure may include a gaze dependent diffractive element, whereby the gaze dependent diffractive element may comprise at least one of the gaze dependent blocking arrangement and/or the gaze dependent shifting arrangement. An exemplary embodiment is described in the following with reference to the drawings.

BRIEF DESCRIPTION OF THE DRAWINGS

The disclosure in the following is described with reference to the drawing, in which

FIG. 9A shows a first realization to induce PRL regions.

FIG. 9B shows a second realization to induce PRL regions.

FIG. 9C shows a third realization to induce PRL regions.

FIG. 15 shows a scheme of prismatic contact lens, in a second realization discouraging a PRL in the left visual field.

FIG. 16A shows a scheme of the gaze contingent training tool.

FIG. 16B shows an example of the realization where the target falls within an area of a bad PRL and is shifted into the preferred region (left half of the visual field).

FIG. 17A shows an electro optic and electrochromic gaze dependent device with a gaze tracker.

DETAILED DESCRIPTION OF EXEMPLARY EMBODIMENTS

Figure 1:
FIG. 1 shows a photography of two children representing a view of a person without any vision loss.
Figure 2:
FIG. 2 shows a simulation of central vision loss.
Figure 3:
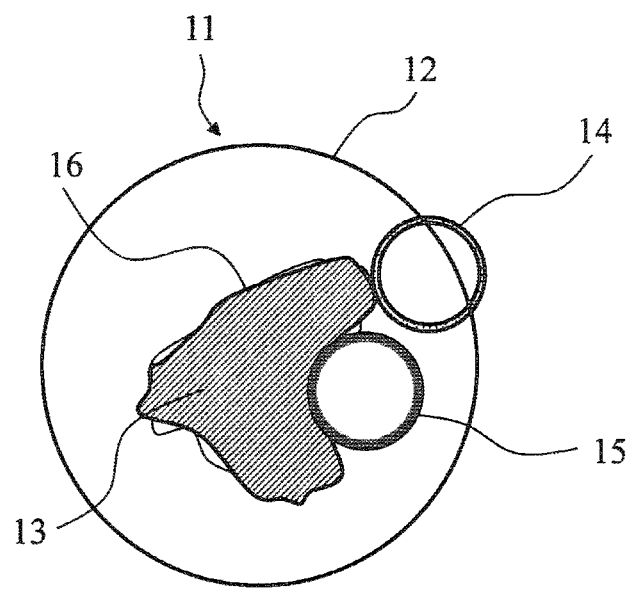
FIG. 3 shows efficient and non-efficient PRLs due to decaying acuity in the periphery.
Figure 4:
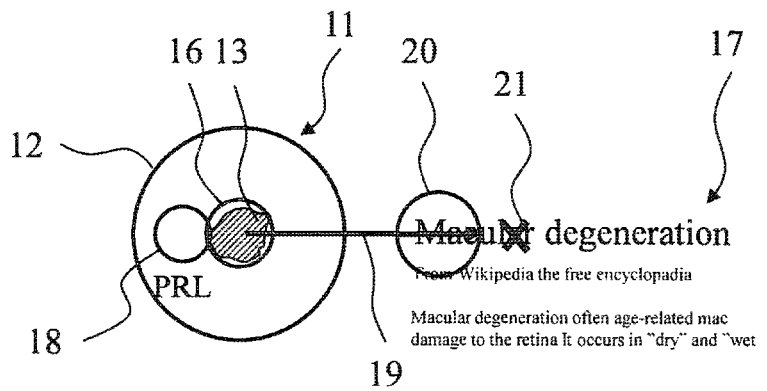
FIG. 4 shows the demonstration of a non-efficient PRL due the direction of reading. The person has to make an eye movement "over" the fixation target (which is the beginning of the word "Macular."
Figure 5:
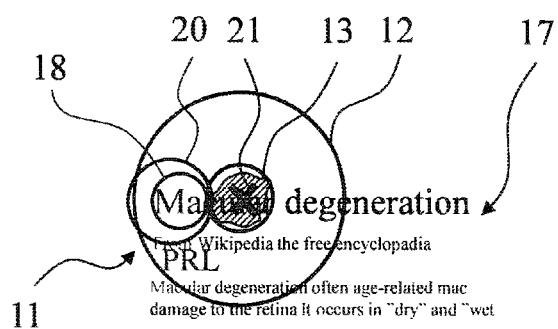
FIG. 5 shows the situation of FIG. 4 after eye movement "over" the fixation target.
Figure 6:
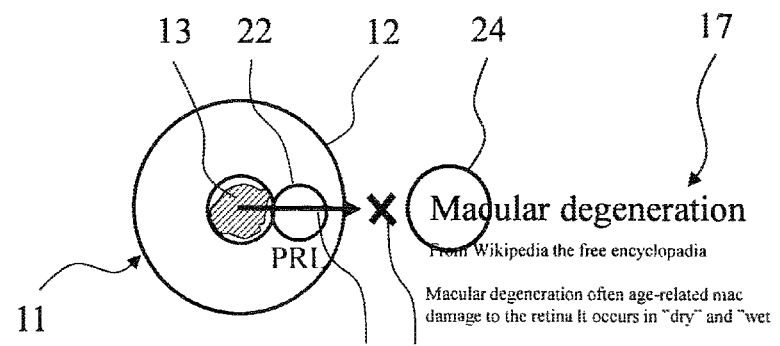
FIG. 6 shows the demonstration of an efficient PRL due the direction of reading. The person has to make an eye movement "before" the fixation target.
Figure 7:
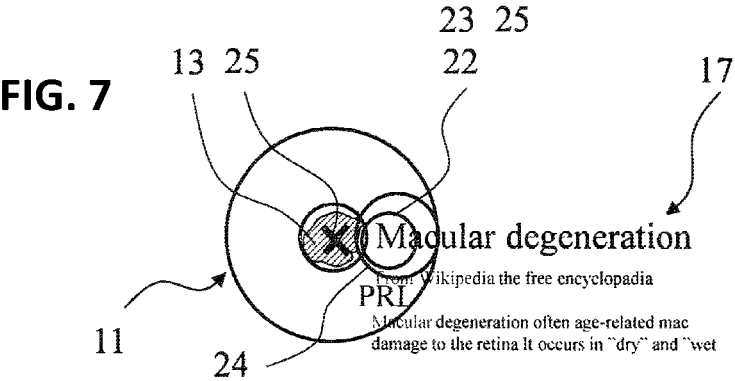
FIG. 7 shows the situation of FIG. 6 after eye movement "before" the fixation target.
Figure 8:
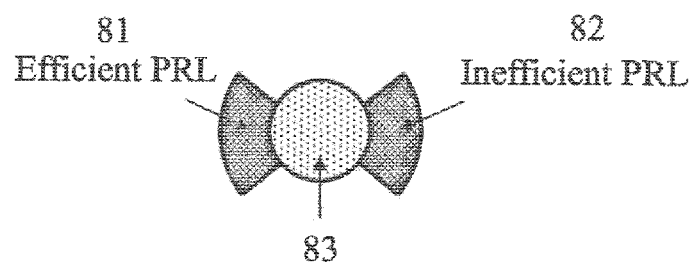
FIG. 8 shows examples of efficient and inefficient PRL regions.

FIG. 8 shows sketched examples of the retina comprising (hypothetical) efficient and inefficient PRL regions 81, 82 being located next to a central scotoma 83. Persons with central vision loss 83 can develop PRL at inefficient regions (e.g., the right-hand sided region 82 in FIG. 8). An aspect of the present disclosure is to induce the location of the PRL at new favorable and efficient regions (e.g., the left-hand side region 81 in FIG. 8).

The realization according to the disclosure is described in the following with reference to FIGS. 9A, 9B, 9C, and 9D. The main strategy used to induce new efficient PRL locations is by discouraging inefficient PRL 82 and encouraging efficient PRL 81 regions.

FIGS. 9A, 9B, and 9C show the three realizations to induce efficient PRLs, respectively. In FIG. 9A, the physiological sketch (left-hand sided drawing) shows the developed undesired PRL 82 (right-hand side as in FIG. 8; the respective former stimulus position is indicated with reference number 94, the stimulus is the letter "A") and the region in which the new PRL 81 is desired to be induced (left-hand side as in FIG. 9A). The three realizations can be summarized as follows:

1. Blocking inefficient PRL regions (the blocked area of the retina is indicated with reference number 92), acts as an extension of the scotoma 83 and blocks visual inputs located at the inefficient PRL regions 82, leaving an unblocked region 91 at an efficient PRL region (represented in FIG. 9A),
2. Blocking inefficient PRL regions (the blocked area of the retina is indicated with reference number 92) and shifting image to the desired region (the shift is indicated with an arrow 93 in the third partial picture) or letting the person chose (two different areas of choice within the unblocked area 91 are indicated with reference numbers 91a and 91b in the fourth partial picture) the region (represented in FIG. 9B),
3. Blocking inefficient PRL regions (the blocked area of the retina is indicated with reference number 92) and partial shift/free choice regions (represented in FIG. 9C).

According to the instant disclosure, a PRL is actively induced at the position most beneficial to the person with central vision loss. This is accomplished by moving the visual information of an eye movement target (the stimulus letter "A" in FIGS. 9A, 9B, 9C, and 9D) from the less efficient RL into the region of an efficient RL.

The principle exploits the fact that eye movements consist of fast, large gaze shifts combined with fixation phases, in which visual information is collected. The point in time, when the person/proband chooses the RL used for fixation is directly after a gaze shift. If now the target falls within an area of a non-efficient PRL, it is shifted into the preferred region for development of a PRL. By doing so, the person/proband is encouraged to develop a PRL in the efficient area of the visual field.

Figure 10:
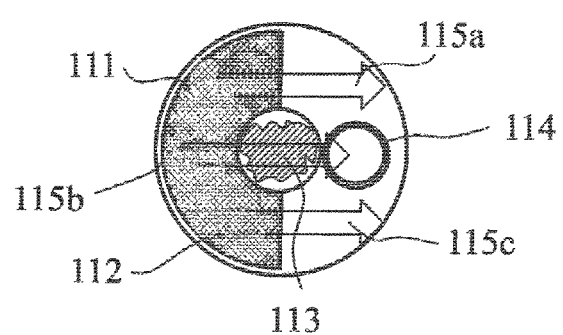
FIG. 10 shows a scheme of PRL induction. At the region of a non-efficient PRL, targets are
  (a) shifted into the region of an efficient PRL.
Figure 9D:
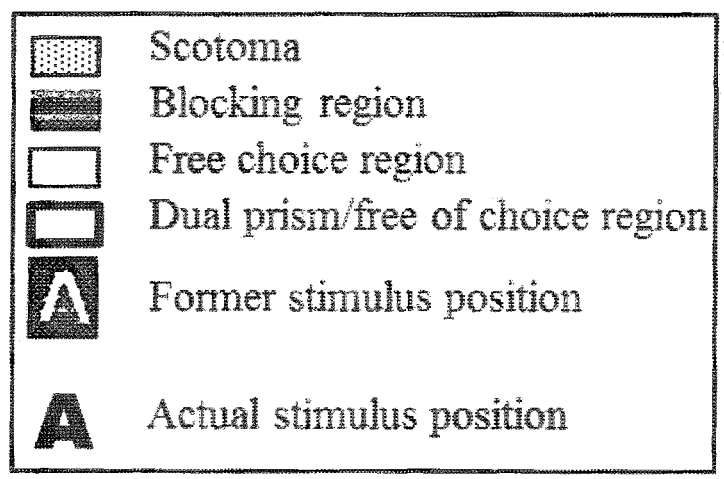
FIG. 9D shows the legend for FIGS. 9A, 9B, and 9C.

FIG. 10 shows a scheme of PRL induction according to the in the foregoing prescribed manner. Shown is the retina with the central scotoma 113 and a region of an efficient PRL 114. At the region of a non-efficient PRL 111 (which in FIG. 10 is even blocked, as indicated by the area 112), targets (such as stimulus letter "A" in FIGS. 9A, 9B, 9C, and 9D) are shifted into the region of an efficient PRL 114, which is indicated by the arrows 115a, 115b, 115c.

Figure 11:
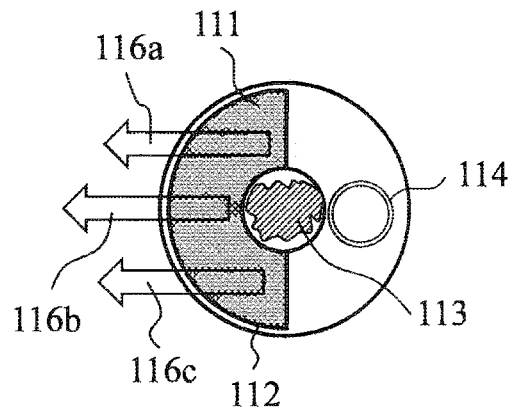
FIG. 11 shows a scheme of PRL induction. At the region of a non-efficient PRL, targets are
  (b) shifted away from the fovea, thus encouraging the person/proband to place the target,
  (c) in the area of an efficient PRL.

In another exemplary embodiment, the non-efficient PRL is discouraged by shifting the target (such as stimulus letter "A" in FIGS. 9A, 9B, 9C, and 9D) away from the fovea. FIG. 11 shows a scheme of PRL induction according to this exemplary embodiment. At the region of a non-efficient PRL 111 (which in FIG. 11 is even blocked, as indicated by the area 112), targets are shifted away from the fovea, thus encouraging the person with scotoma 113 to place the target in the area of an efficient PRL 114.

Figure 12:
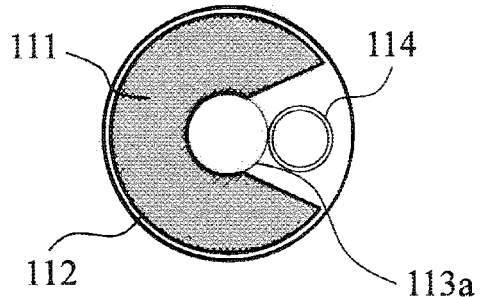
FIG. 12 shows a scheme of PRL induction. At the region of a non-efficient PRL, the target information is blocked, thus encouraging the person to place the target in the area of an efficient PRL.
Figure 13:
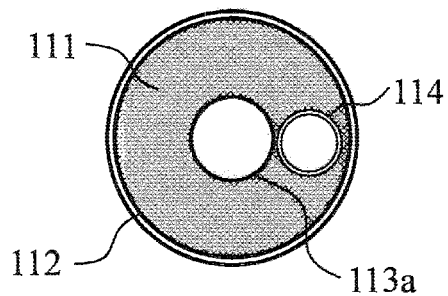
FIG. 13 shows another scheme of PRL induction. At the region of a non-efficient PRL, the target information is blocked, thus encouraging the person to place the target in the area of an efficient PRL.

In another exemplary embodiment, the visual information (stimulus letter "A" in FIGS. 9A, 9B, 9C, and 9D) is not shifted, but instead blocked in a ring-shaped area 112 around the field loss 113a. FIGS. 12 and 13 show such schemes of PRL induction. It may be worth mentioning that blocking of the area of the field loss 113a is not required but possible since the person does not perceive information from the area anyhow. In addition, the term ring-shaped as used herein does not require a circular outer (or even inner) border line. Ring shaped means a shape being capable of blocking at least a part of the "mainly non-disturbed" visual field surrounding the scotoma 113 (which may comprise that the region of the scotoma 113, 113a itself is also blocked).

At the region of a non-efficient PRL, target information is blocked, thus encouraging the person to place the target in the area of an efficient PRL.

The exact shape of the ring (its thickness and the open angle) can be varied. Thus, even a pinhole-like training tool (see in particular FIG. 13) can be designed.

Figure 14:
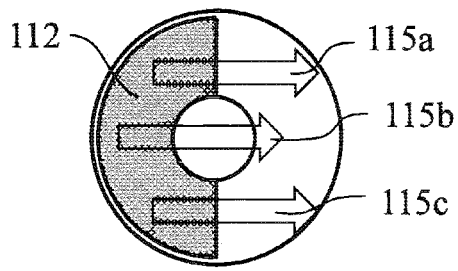
FIG. 14 shows a scheme of prismatic contact lens, in a first realization discouraging a PRL in the left visual field.

As already indicated when discussing FIGS. 10 (and 11) above, both blocking with a ring-shaped area 112 surrounding the scotoma and shifting (reference numbers 115a, 115b, 115c, 116a, 116b, 116c) in order to encourage or discourage PRLs is possible, which is shown in FIGS. 14 and 15.

Technically, this training can be performed in several different ways:

Gaze-Contingent Training Tool

In this gaze-contingent system the person/proband is viewing stimuli (such as several well-separated letters or short words) on a presentation screen. If provided with a high-quality eye tracker, this screen can also be a video-enabled, head mounted display, such as a device sold by the applicant under the trade name VR One. Another implementation is a gaze-contingent electro-optical device, where a prism can be switched on and off in real-time. Whenever the person is eliciting an eye-movement that brings one of the targets into a non-efficient region for a PRL (such as the dark area in FIG. 10), the target will be shifted. Thus, it will be presented in the preferred region of a PRL. The person/proband will adopt his behavior in two ways. First, he will use this preferred region to identify the target. Furthermore, he will try to elicit future eye movements directly in a way, which bring the target into the area of the efficient PRL.

FIGS. 16A and B show an example of such a gaze-contingent training tool. FIG. 16A shows the principle by means of a scheme, FIG. 16B shows two images 162a-1, 162a-2 of a presentation screen/display 162a. The gaze-contingent training tool comprises a gaze tracker 161 for tracking the gaze of the person/proband (eyes of the person/proband indicated by reference number 163a, 163b, a computer 162 for analyzing the tracked gaze of the person/proband and for controlling the position and content of a target 162b being presented to the person/proband on a respective computer screen or display 162a. FIG. 16B shows that in the first image 162a-1 the target 162b is located at a different position indicated by reference number 162b-1 than the position indicated by reference number 162b-1 in the second image 162a-2.

The first image 162a-1 shows the situation when the actual person/proband's gaze (represented by the scotoma 113) moves via the display 162a in order to bring the displayed target 162b-1 into the visual field. The movement of the gaze is indicated with the arrow 181.

In this exemplary embodiment, the efficient PRL is assumed to be on the left-hand side of the scotoma 113, while the inefficient PRL is assumed to be on the right-hand side of the scotoma 113. In order to avoid that the person/proband uses the visual field on the retina on the right-hand side of the scotoma 113, the right-hand side of the visual field has to be blocked. Taking into consideration the tracked position of gaze on the computer screen 162a provided by the computer-performed analysis of the tracked gaze by means of the gaze tracker 161, the respective region corresponding to the right-hand side to the actual position of the disturbed visual field on the computer screen 162a may be hidden (blocked), which is indicated by the region 112 for demonstration purposes. This region 112 will typically not be visible to the person/proband and will therefore have the same color as the background on which the target 162b is shown.

After movement 181 of the gaze, the presented target 162b is not visible anymore since it is blocked (hidden) because it is located within region 112 as is shown in the image 162a-2. In order to encourage the person/proband to use his/her efficient PRL, which is located left to the scotoma 113, the target is "shifted," or more concretely displayed instead in a region of the computer screen 162a which corresponds to the left-hand side to the region corresponding to the scotoma 163 of the visual field, which is momentarily hit on the computer screen 162a due to the present direction of gaze. The "shift" of the target 162b is indicated with arrow 182. The position of the target 162b after the "shift" is indicated with reference number 162b-2.

It shall be mentioned that herein "shift to another location" does not only have the meaning of "move to another location," but also the meaning "display at another location." In addition, "blocking" herein does not only have the meaning of "actively eliminating," but also the meaning "hiding" or "making invisible."

Prismatic Contact Lens

The same behavior can be evoked by a locally prismatic contact lens. The contact lens will have a prism at the areas of non-efficient regions for a PRL. The prismatic region of the contact lens can be manufactured either refractive, but also diffractive. FIGS. 14 and 15 show a scheme of a prismatic contact lens, in two different exemplary embodiments for discouraging a PRL in the left visual field.

Figure 20A:
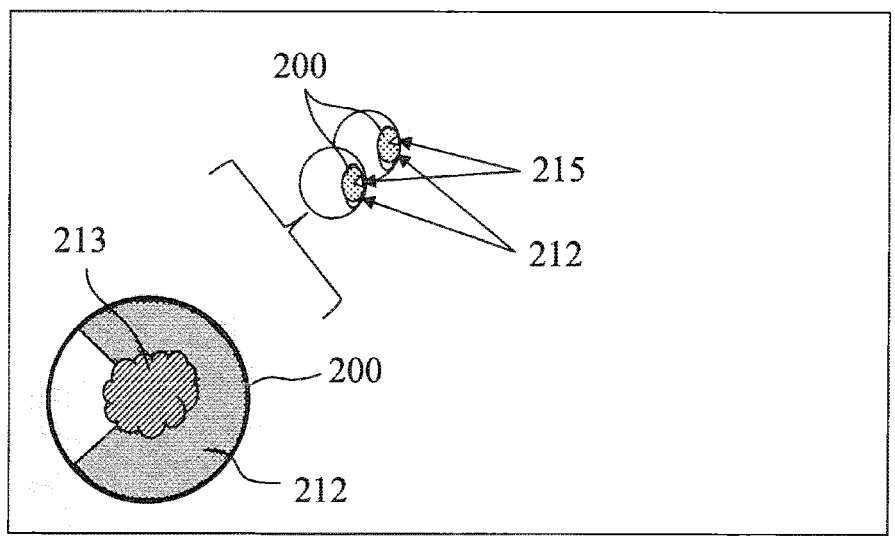
FIG. 20A shows a contact lens with prismatic and blocking function.

There may be a contact lens with prismatic (represented by the shifts 115a, 115b, 115c, 116a, 116b, 116c in FIGS. 14 and 15) and blocking (represented by the region 112) function. The training will be performed with a stimulus presented at a reading distance on a sheet of paper. FIG. 20A shows such a contact lens 200 with prismatic and blocking function. The prismatic power is indicated with reference number 215, the blocking regions are indicated with reference number 212. The position of the scotoma 213 behind the contact lens is also indicated in FIG. 20A.

Intraocular Lens (IOL)

The same behavior can be evoked by a locally prismatic or blinded contact lens. In this case, it is beneficial to apply a technique where the prism is only existing temporally in the IOL during the training period.

Figure 20B:
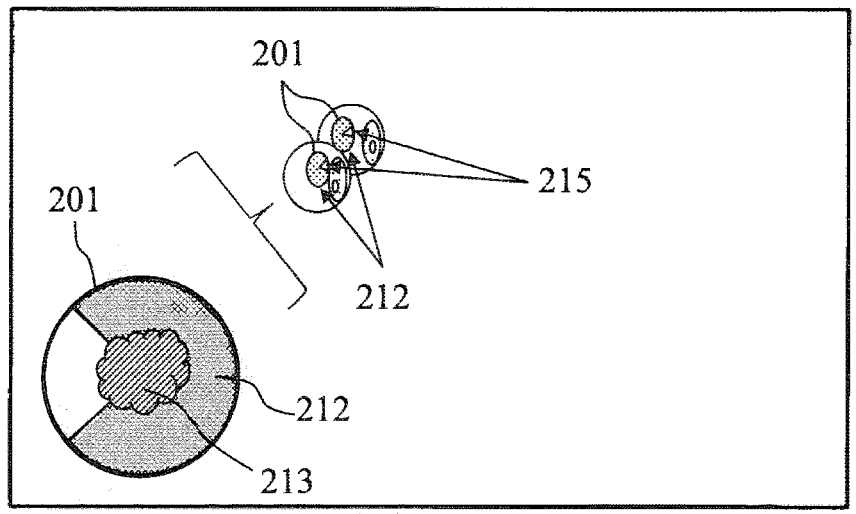
FIG. 20B shows an intraocular lens with prismatic and blocking function.

For such an intraocular lens with prismatic and blocking function, the training will be performed with a stimulus presented at a reading distance on a sheet of paper. FIG. 20B shows such an intraocular lens 201 with prismatic and blocking function. The prismatic power is indicated with reference number 215, the blocking regions are indicated with reference number 212. The position of the scotoma 213 behind the contact lens is also indicated in FIG. 20B.

Electrochromic Device

In an exemplary embodiment in which only blocking occurs, the blocking can be realized via an electrochromic device, which blocks transmission in the nonefficient PRL-areas.

Figure 21A:
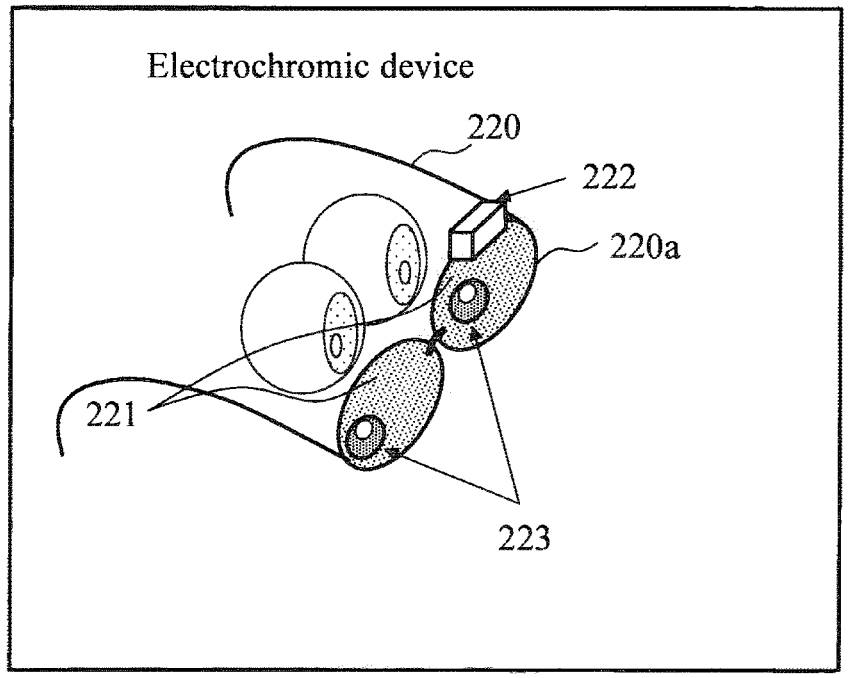
FIG. 21A shows an electrochromic spectacle with gaze tracker.
Figure 21B:
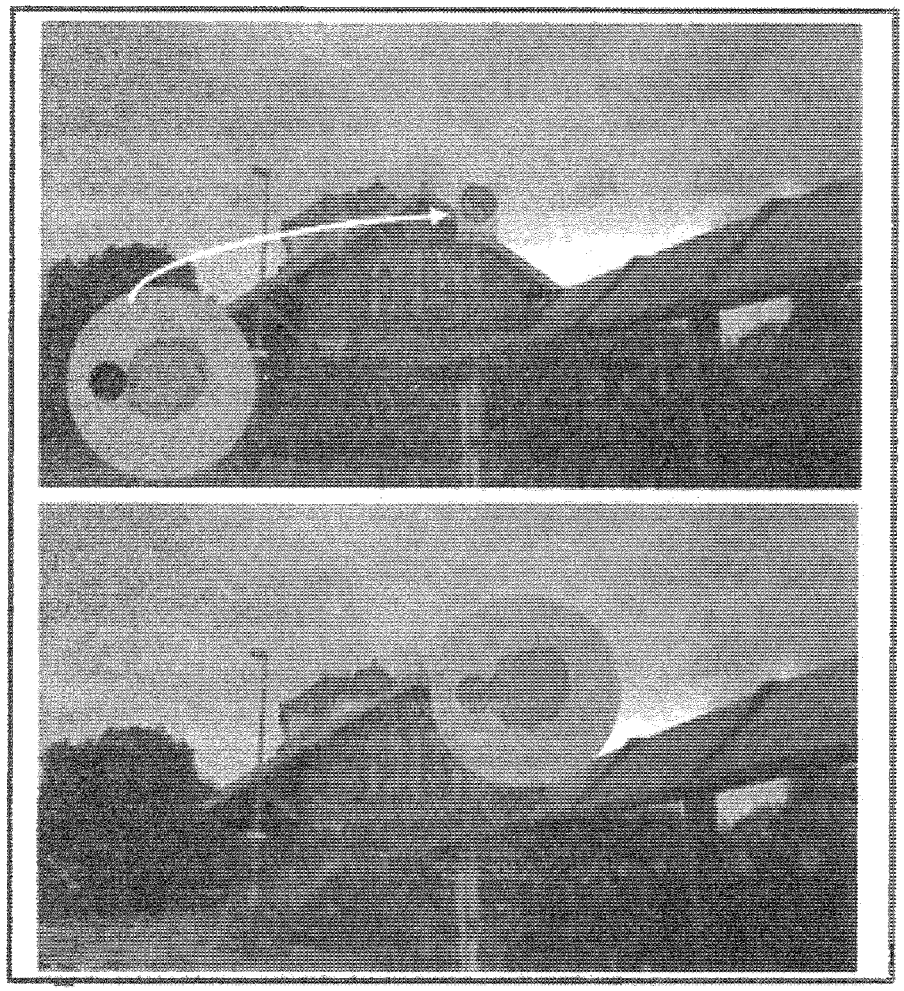
FIG. 21B shows an example of viewing of natural images with the electro chromic gaze dependent device according to FIG. 21A. In this example, the subject uses the window to see the object under interest.

There may also exist embodiments combining an electrochromic and gaze tracking device as is shown, e.g., in FIG. 21A. The device according to FIG. 21A comprises spectacles 220 having spectacle lenses 221 with gaze dependent photochromic blocking regions 223 and a gaze tracker 222 mounted onto the frame 220a of the spectacles 220. FIG. 21B shows an example of viewing of natural images with such an electrochromic gaze dependent device shown in FIG. 21A. In this example, the subject uses the window to see the object under interest.

Electro-Optical Device

In a specifically flexible exemplary embodiment, prismatic and light blocking optical properties are realized in an electro-optical device. This might be positioned either eye-centric (as a contact lens), or head-centric (as a spectacle), were gaze tracking is applied to determine the retinal locations where information should be blocked or shifted.

Figure 17B:
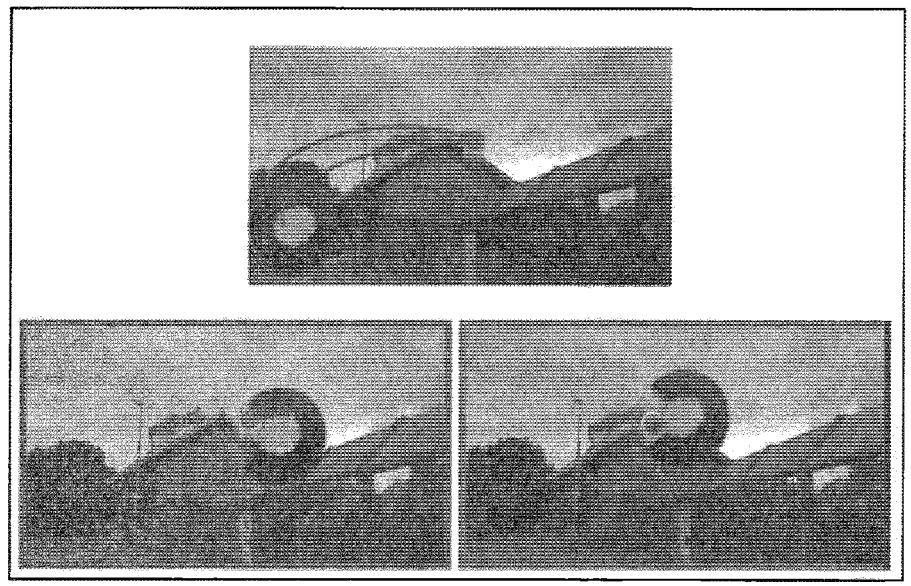
FIG. 17B shows the two possible eye movements (upper picture) and their inducing consequence by shifting or by freely locating the target on the desired area (lower pictures).

FIG. 17A shows an electro optic-electrochromic device with gaze tracker. FIG. 17B shows the two possible eye movements (upper picture) and their inducing consequence by shifting or by freely locating the target on the desired area (lower pictures). The device according to FIG. 17A comprises spectacles 320 having spectacle lenses 321 with gaze dependent electrochromic blocking regions 323, gaze dependent electro-optic prismatic power 324, and a gaze tracker 322 mounted onto the frame 320a of the spectacles 320. The momentary relevant areas with gaze controlled electro optic prismatic power 324 and gaze controlled electrochromic blocking function 323 are indicated with reference number 325. For completeness reasons, the position of the scotoma 313 is indicated in FIG. 17A as well.

Refractive or Diffractive

Figure 18:
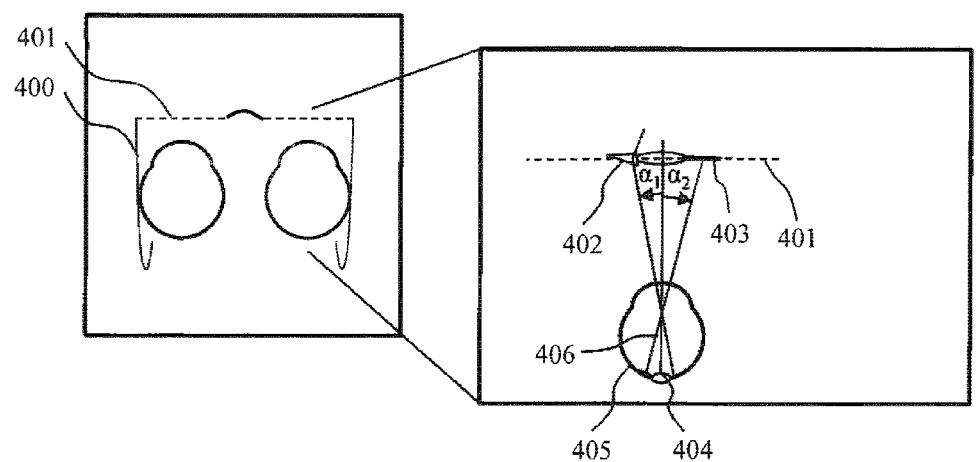
FIG. 18 shows a gaze dependent diffractive spectacle. On the right, the image shows at a fixed gaze the two components of the spectacle and their respective consequence on the retina. The prismatic component brings the image to the desired retinal location and the blocking component blanks the image at the non-desired retinal location.

Especially the prismatic functions, but also other required functions might be realized in a diffractive way. Furthermore, in a diffractive realization, the wavelength spectrum of the unmodified areas can be selectively filtered to provide maximum contrast and/or to block harming blue wavelengths. FIG. 18 shows a diffractive spectacle 400 comprising a diffractive element 401 with two main components, a prismatic component 402 and a blocking component 403, both gaze angle dependent. On the right side of FIG. 18, the image shows at a fixed gaze the two components 402, 403 of the spectacle 400 and their respective consequence on the retina 404 of an eye 405 of a person/proband which is rotatable about its center of rotation 406. The prismatic component 402 brings the image to the desired retinal location and the blocking component 403 blanks the image at the non-desired retinal location.

Figure 19:
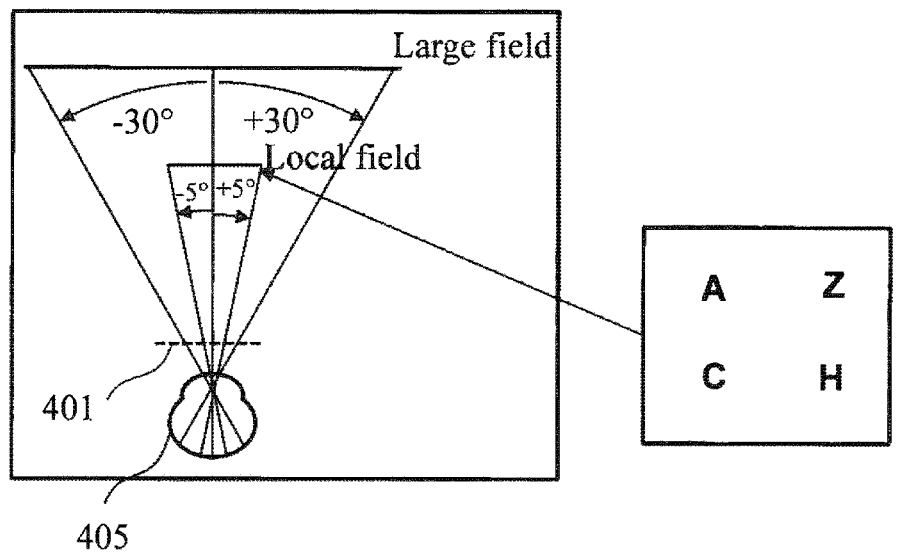
FIG. 19 shows large and local field view and example of presented stimuli.

The previous solution can be applied in two different field of view sizes as shown in FIG. 19:

Large field: stimuli presented on a display.

Local field: stimuli presented at a reading distance in a cellphone.

Head Mounted Display (HMD) and Gaze Tracker:

This tool may provide training using live video imaging or stimuli. In training using live video, imaging of a natural scene is presented and an algorithm makes realization 1, 2, and 3 described above possible. Using stimuli, the training is carried out as in solution 1.

Training Procedure:

The training can be applied monocularly or binocularly. In monocular training the second (in most cases healthy) eye is covered. If both eyes are affected, a common efficient PRL is defined.

The training should be applied in several sessions (e.g., daily for 30 minutes over a period of 2 weeks).

In case the area of vision loss increases and covers the induced PRL, the training can also be reapplied to induce a new PRL.

Standard Solution

Generally, a PRL in the right visual field might be beneficial, thus the solution depicted in FIG. 10 or 11 can be considered standard solutions (because of the direction of reading).

Customized Solutions

But, to determine the size of the area of vision loss, perimetry applies. In the realization of the gaze contingent training tool (see A. above), the training device can be used as perimetry device, too. It can show test lights in a determined position relative to the gaze position. Thus, the exact power of the prism applied and the exact direction of the shift can be determined. In case a flexible realization (electrochromic device, electro-optical device) is used (see, e.g., D. and E. above), the optical properties needed to induce the PRL at the most efficient position can be determined at regular intervals if necessary. Together with an automated workflow this might even be done by the person/proband himself. The decision criteria for the application of the optical function are the above mentioned (as close as possible to the fovea, preferred position in the right visual field).

Summarizing the main idea of the disclosure the following clauses are provided which shall be part of the description:

1. Method, in particular computer-implemented method, for training a preferred retinal locus of fixation for a person having an eye with a field of vision comprising an area of partially diminished or entirely degenerated visual acuity comprising the steps:

determining an inefficient retinal region in the field of vision of the eye of the person inducing a preferred retinal locus of fixation for a vision task outside the inefficient retinal region.

2. Method according to clause 1, whereby the step inducing a preferred retinal locus of fixation for the vision task outside the inefficient retinal region comprising the step:

blocking the inefficient retinal region for the vision task.

3. Method according to clause 1 or 2, further comprising the step:

providing a fixation target for the vision task to the person.

4. Method according to clause 3, further comprising the step: shifting the fixation target to an unblocked region outside the blocked inefficient retinal region.

5. Method according to clause 4, whereby the step of shifting the fixation target to an unblocked region outside the blocked inefficient retinal region comprising the step:

shifting the fixation target from the blocked inefficient retinal region to an efficient retinal region.

6. Method according to clause 4, whereby the field of vision comprising a foveal region, and whereby the step of shifting the fixation target to an unblocked region outside the blocked inefficient region comprising the step:

shifting the fixation target from the blocked inefficient region away from the foveal region.

7. Method according to one of clauses 2 to 6, comprising the steps:

tracking a gaze of the eye during conducting the vision task, determining the inefficient retinal region to be blocked based on the tracked gaze and/or determining the region the fixation target to be shifted to based on the tracked gaze.

8. Method according to one of the preceding clauses, whereby the step determining an inefficient retinal region in the field of vision of the eye of the person for the vision task comprising the steps:

determining an efficient retinal region in the field of vision of the eye of the person for the vision task, setting a region outside the efficient retinal region in the field of vision of the eye of the person for the vision task as defining the inefficient retinal region in the field of vision of the eye of the person for the vision task.

9. Method according to one of clauses 3 to 8, whereby the step blocking the inefficient retinal region when providing the fixation target to the person for conducting the vision task comprising one or more of the following steps:

hiding a region of the fixation target corresponding to the inefficient retinal region when providing the fixation target to the person for conducting the vision task, exclusively revealing a region of the fixation target corresponding to a region outside the inefficient retinal region when providing the fixation target to the person for conducting the vision task, and exclusively presenting a region of the fixation target corresponding to a region outside the inefficient retinal region when providing the fixation target to the person for conducting the vision task.

10. Method according to one of the preceding clauses, comprising the step:

at least partially blocking the area of entirely degenerated visual acuity, preferably fully blocking the area of entirely degenerated visual acuity.

11. Device for training a preferred retinal locus of fixation for a person having an eye with a field of vision comprising an area of partially diminished or entirely degenerated visual acuity whereby an inducing arrangement for inducing a preferred retinal locus of fixation for a vision task outside an inefficient retinal region in the field of vision of the eye of the person.

12. Device according to clause 11, whereby at least one of a gaze dependent blocking arrangement for blocking an area of the visual field dependent on direction of gaze of the eye, and a gaze dependent shifting arrangement for shifting a fixation target dependent on direction of gaze of the eye.

13. Device according to clause 12, whereby a gaze tracking arrangement for tracking a gaze of the eye during conducting a vision task, and at least one of a control arrangement for controlling the area of the visual field to be blocked based on the tracked gaze of the eye, and a control arrangement for controlling the shifting of the fixation target based on the tracked gaze of the eye.

14. Device according to one of clauses 12 to 13, whereby the gaze dependent shifting arrangement comprising or consisting in a gaze dependent prismatic arrangement.

15. Device according to one of clauses 12 or 14, whereby at least one of the blocking arrangement and the shifting arrangement being detachably fixed to the eye.

16. Device according to one of clauses 12 to 15, comprising a gaze dependent diffractive element, whereby the gaze dependent diffractive element comprising at least one of the gaze dependent blocking arrangement and the gaze dependent shifting arrangement.

17. Computer program with program code to execute the method steps according to one of the clauses 1 to 10, if the computer program is loaded in the computer and/or executed in the computer.

The foregoing description of the exemplary embodiments of the disclosure illustrates and describes the present disclosure. Additionally, the disclosure shows and describes only the exemplary embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The term "comprising" (and its grammatical variations) as used herein is used in the inclusive sense of "having" or "including" and not in the exclusive sense of "consisting only of." The terms "a" and "the" as used herein are understood to encompass the plural as well as the singular.

All publications, patents and patent applications cited in this specification are herein incorporated by reference, and for any and all purposes, as if each individual publication, patent or patent application were specifically and individually indicated to be incorporated by reference. In the case of inconsistencies, the present disclosure will prevail.

The invention claimed is:

1. A computer program stored on a non-transitory storage medium with program code to execute a method for training a preferred retinal locus of fixation for a person having an eye with a field of vision including an area of partially diminished or entirely degenerated visual acuity when the computer program is loaded in a computer or executed in the computer, the method comprising:

determining an inefficient retinal region (Inefficient PRL) for a specific vision task outside an area (Central Scotoma) of a partially diminished or entirely degenerated visual acuity in a field of vision of an eye of a person and a more efficient retinal region (Efficient PRL) for the specific vision task outside the area (Central Scotoma) of the partially diminished or entirely degenerated visual acuity in the field of vision of the eye of the person, detecting, with an eye tracker, a gaze shift and a fixation phase of the eye of the person, inducing a preferred retinal locus of fixation (Efficient PRL) for the specific vision task outside the inefficient retinal region (Inefficient PRL), but in the more efficient retinal region (Efficient PRL) by shifting the retinal locus of fixation from the inefficient retinal region outside the area onto the more efficient retinal region outside the area, whereby the inducing the preferred retinal locus of fixation (Efficient PRL) for the specific vision task outside the inefficient retinal region (Inefficient PRL), but in the more efficient retinal region (Efficient PRL) comprises one or both of:

providing a fixation target for the specific vision task to the person to encourage the person to move a head, an eye, or the head and the eye to gaze with the retinal location of fixation of the eye of the person lying outside the inefficient retinal region (Inefficient PRL), or blocking the inefficient retinal region (Inefficient PRL) for the specific vision task to discourage the person to move the head, the eye, or the head and the eye to gaze in a direction with the retinal location of fixation of the eye of the person lying inside the inefficient retinal region (Inefficient PRL), wherein the providing the fixation target and/or the blocking of the inefficient retinal region (Inefficient PRL) is performed with a gaze-contingent training tool in response to the detected gaze shift.

2. The computer program according to claim 1, further comprising:

shifting the fixation target to an unblocked region outside a blocked inefficient retinal region.

3. The computer program according to claim 2, wherein the shifting the fixation target to the unblocked region outside the blocked inefficient retinal region comprises:

shifting the fixation target from the blocked inefficient retinal region to the efficient retinal region.

4. The computer program according to claim 2, wherein the field of vision comprises a foveal region, and wherein the shifting the fixation target to the unblocked region outside the blocked inefficient region further comprises:

shifting the fixation target from the blocked inefficient region away from the foveal region.

5. The computer program according to claim 1, further comprising:

tracking the gaze of the eye during the conducting the specific vision task, and determining the inefficient retinal region (Inefficient PRL) to be blocked based on the tracked gaze and/or determining the region for the fixation target to be shifted to based on the tracked gaze.

6. The computer program according to claim 1, wherein the determining the inefficient retinal region (Inefficient PRL) in the field of vision of the eye of the person for the vision task further comprises:

determining an efficient retinal region (Efficient PRL) in the field of vision of the eye of the person for the vision task, and setting a region outside the efficient retinal region (Efficient PRL) in the field of vision of the eye of the person for the vision task as defining the inefficient retinal region (Inefficient PRL) in the field of vision of the eye of the person for the vision task.

7. The computer program according to claim 1, wherein the blocking the inefficient retinal region (Inefficient PRL) when providing the fixation target to the person for conducting the specific vision task comprises one or more of following:

hiding a region of the fixation target corresponding to the inefficient retinal region (Inefficient PRL) when providing the fixation target to the person for conducting the specific vision task, exclusively revealing a region of the fixation target corresponding to a region outside the inefficient retinal region (Inefficient PRL) when providing the fixation target to the person for conducting the specific vision task, or exclusively presenting a region of the fixation target corresponding to the region outside the inefficient retinal region (Inefficient PRL) when providing the fixation target to the person for conducting the specific vision task.

8. The computer program according to claim 1, further comprising:

at least partially blocking the area (Central Scotoma) of the entirely degenerated visual acuity.

9. The computer program according to claim 8, further comprising:

fully blocking the area (Central Scotoma) of the entirely degenerated visual acuity.

10. A device for training a preferred retinal locus of fixation for a person having an eye with a field of vision comprising an area (Central Scotoma) of partially diminished or entirely degenerated visual acuity, the device comprising:

a gaze tracking arrangement for tracking a gaze shift and a fixation phase of the eye conducting a specific vision task, an inducing arrangement containing a display and being configured to induce a preferred retinal locus of fixation (Efficient PRL) for the specific vision task by shifting the retinal locus of fixation from a predetermined inefficient retinal region (Inefficient PRL) for the specific vision task outside the area (Central Scotoma) of a partially diminished or entirely degenerated visual acuity in a field of vision of an eye of a person, but onto a predetermined more efficient retinal region (Efficient PRL) for the specific vision task outside the area (Central Scotoma) of the partially diminished or entirely degenerated visual acuity in the field of vision of the eye of the person, whereby the inducing arrangement for inducing the preferred retinal locus of fixation for the specific vision task outside the predetermined inefficient retinal region (Inefficient PRL) but onto the predetermined more efficient retinal region (Efficient PRL) comprises a gaze-contingent training tool having one or both of:

a gaze dependent shifting arrangement for shifting a fixation target dependent on the direction of gaze of the eye to encourage the person to move a head, an eye, or the head and the eye to gaze with the retinal location of fixation of the eye of the person lying outside the predetermined inefficient retinal region (Inefficient PRL), or a gaze dependent blocking arrangement for blocking an area of the visual field dependent on a direction of gaze of the eye to discourage the person to move the head, the eye, or the head and the eye to gaze in a direction with the retinal location of fixation of the eye of the person lying inside the predetermined inefficient retinal region (Inefficient PRL), wherein the shifting of the fixation target and/or the blocking the area of the visual field dependent on a direction of gaze of the eye is performed in response to the detected gaze shift.

11. The device according to claim 10, wherein at least one of:

the gaze dependent blocking arrangement is configured to block the predetermined inefficient retinal region for the specific vision task dependent on the direction of gaze of the eye, or the gaze dependent shifting arrangement is configured to shift the fixation target to an unblocked region outside the predetermined inefficient retinal region (Inefficient PRL) for the specific vision task dependent on the direction of gaze of the eye.

12. The device according to claim 10, wherein the shifting comprises moving a visual information of the fixation target from the predetermined inefficient retinal region for the specific vision task into an efficient retinal region (Efficient PRL) for the specific vision task or into a region being completely outside the visual field.

13. The device according to claim 10, further comprising at least one of:

a control arrangement for controlling the area of the visual field to be blocked based on the tracked gaze of the eye, or a control arrangement for controlling the shifting of the fixation target based on the tracked gaze of the eye.

14. The device according to claim 10, wherein the gaze dependent shifting arrangement comprises or consists of a gaze dependent prismatic arrangement.

15. The device according to claim 10, further comprising:

a gaze dependent diffractive element, wherein the gaze dependent diffractive element includes at least one of the gaze dependent blocking arrangement and the gaze dependent shifting arrangement.

* * * * *